United States Patent [19]

Bilstad et al.

[11] Patent Number: 4,498,983

[45] Date of Patent: Feb. 12, 1985

[54] PRESSURE CUFF DRAW MODE ENHANCEMENT SYSTEM AND METHOD FOR A SINGLE NEEDLE BLOOD FRACTIONATION SYSTEM

[75] Inventors: Arnold C. Bilstad, Deerfield; John T. Foley, Wheeling; Walker P. Woodworth, Vernon Hills, all of Ill.

[73] Assignee: Baxter Travenol Laboratories, Inc., Deerfield, Ill.

[21] Appl. No.: 498,583

[22] Filed: May 26, 1983

[51] Int. Cl.³ .............................................. A61M 5/00
[52] U.S. Cl. ..................................... 210/97; 210/143; 604/6
[58] Field of Search ............... 210/744, 927, 104, 128, 210/DIG. 6, 97, 143, 96.1, 96.2; 129; 604/4, 9, 6

[56] References Cited

U.S. PATENT DOCUMENTS

| | | | |
|---|---|---|---|
| 3,489,145 | 1/1970 | Judson et al. | 128/214 A |
| 4,086,924 | 5/1978 | Latham, Jr. | 233/1 X |
| 4,137,168 | 1/1979 | Merrot | 210/104 |
| 4,397,747 | 8/1983 | Ikera | 210/104 |

FOREIGN PATENT DOCUMENTS 44694  1/1982  European Pat. Off. .

Primary Examiner—John Adee

Attorney, Agent, or Firm—Paul C. Flattery; Daniel D. Ryan; Eugene M. Cummings

[57] ABSTRACT

A pressure cuff draw mode enhancement system for a blood fractionation system having a single-lumen phlebotomy needle, a flow-through plasma separation filter, and an in-process fluid reservoir, includes a pressure cuff in operative association with the donor. During an initial draw cycle of the system whole blood is pumped by an inlet pump through the filter to the in-process reservoir. When a predetermined volume of filtered plasma-deficient blood has been collected in the reservoir, as sensed by the weight of the reservoir, the system reverts to a return cycle wherein a portion of the plasma-deficient blood in the reservoir is pumped back to the phlebotomy needle by a return pump. Depending on the relative operating rates of the inlet and return pumps, an operator-controllable portion of the plasma-deficient blood from the in-process reservoir is returned to the donor through the phlebotomy needle, and the remaining portion is recirculated through the filter. To facilitate higher whole blood draw rates, the pressure cuff draw mode enhancement system pressurizes the pressure cuff during each draw cycle. Upon completion of the draw cycle, the pressure cuff is depressurized to facilitate the return of blood to the donor during the succeeding return cycle. A safety circuit prevents operation of the return pump unitl the pressure cuff has adequately depressurized.

8 Claims, 14 Drawing Figures

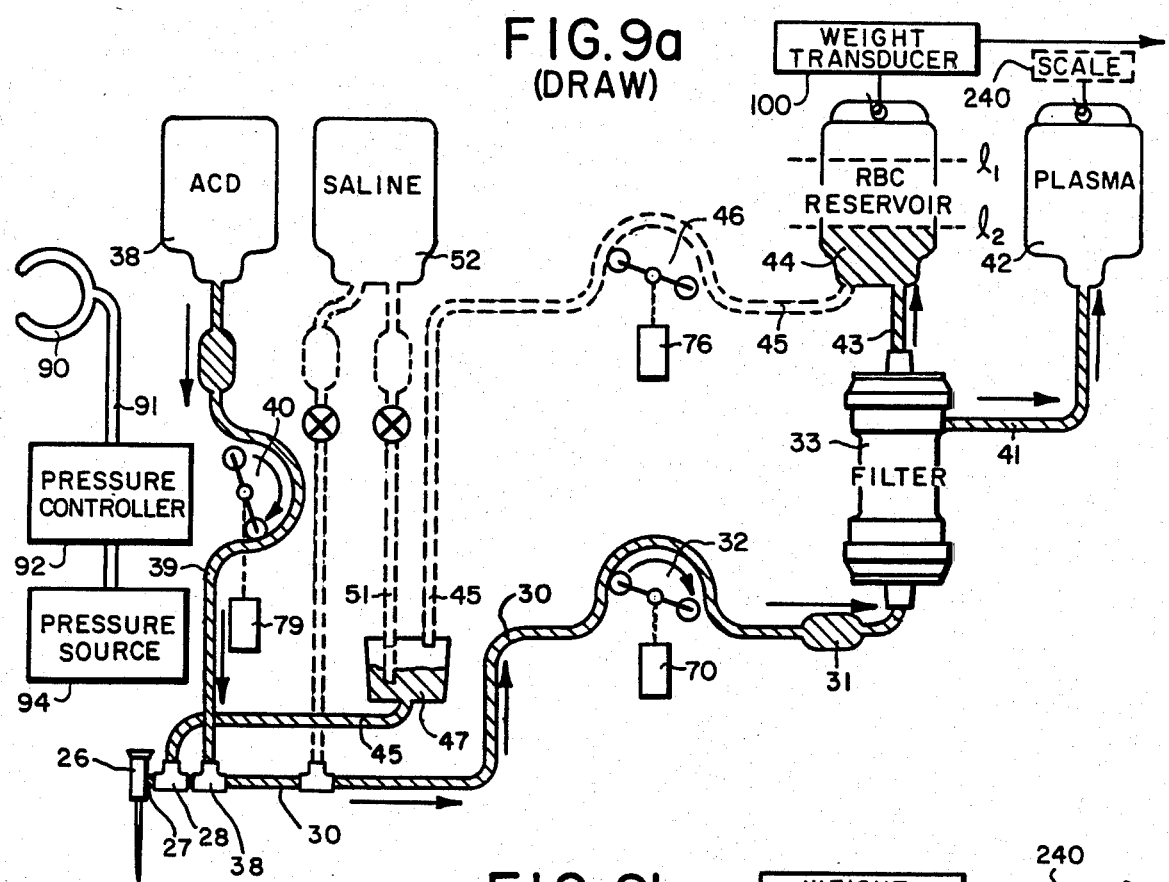

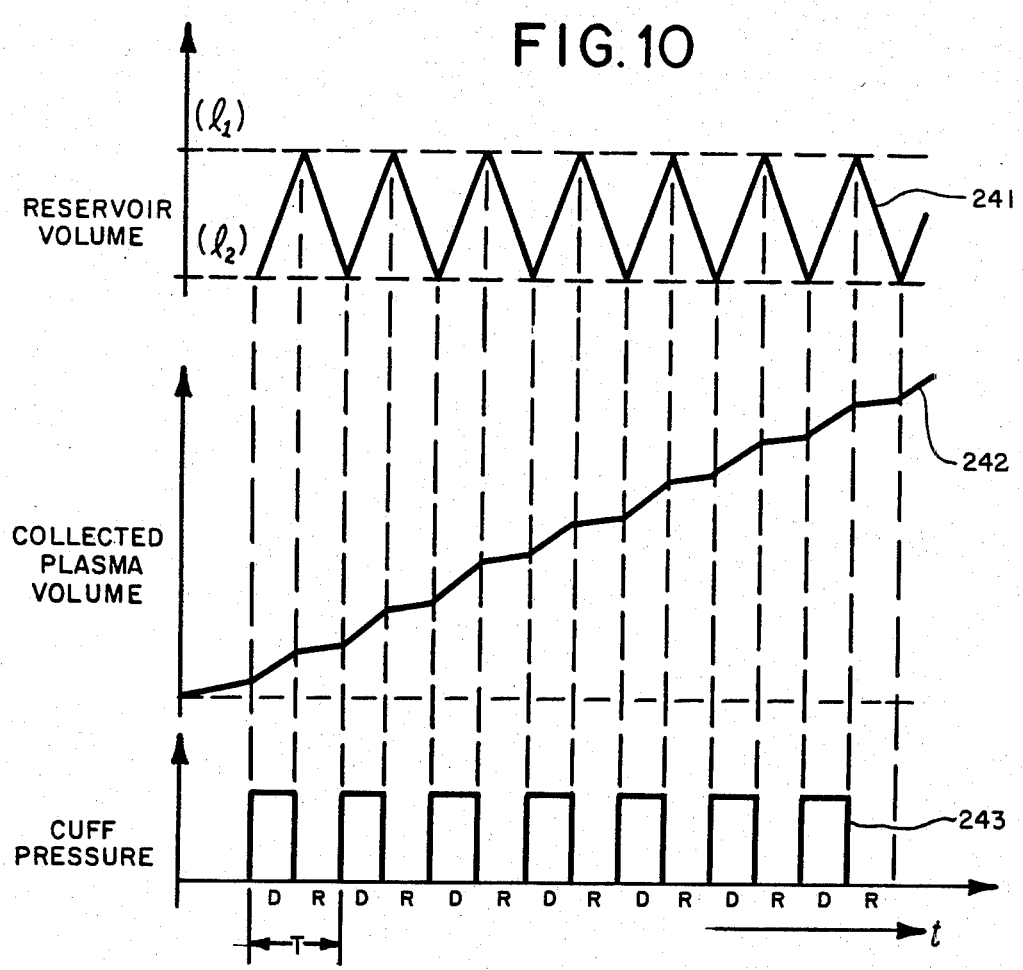
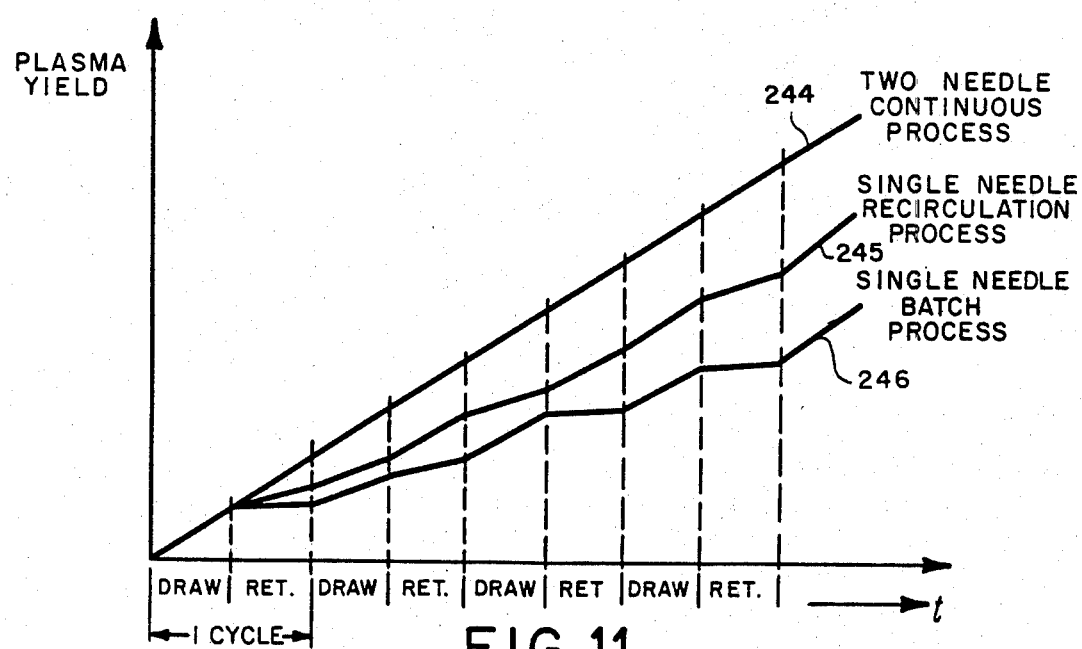

PRESSURE CUFF DRAW MODE ENHANCEMENT SYSTEM AND METHOD FOR A SINGLE NEEDLE BLOOD FRACTIONATION SYSTEM

BACKGROUND OF THE INVENTION

The present invention relates generally to systems and apparatus for processing whole blood, and more specifically to a pressure cuff draw mode enhancement system and method for a single needle in vivo blood fractionation apparatus.

Various methods and apparatus have been developed for the in vivo processing of whole blood, wherein the whole blood is taken from a donor, a desired blood component is separated and collected, and the processed blood is returned to the donor. Blood components typically collected using such processing include plasma (plasmapheresis), white blood cells (leukopheresis) and platelets (plateletpheresis).

In vivo blood processing apparatus may be of the centrifugal type, wherein the differing density of the collected blood component causes the component to congregate for collection at a particular radial distance in a centrifuge, or may be of the filter type, wherein the particle size of the collected component allows only that component to pass through a filter membrane into a collection chamber. Filter type apparatus is generally preferable for in vivo plasmapheresis applications, since such apparatus does not require complex rotating machinery and is more compact and less costly to manufacture.

One form of filter which is particularly attractive for use in plasmapheresis apparatus utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collection chamber from which the component is transported to a collection container. A preferred construction and method of manufacture of such a flow-through hollow fiber filter is shown in the copending application of Robert Lee and William J. Schnell entitled, "Microporous Hollow Fiber Membrane Assembly and Its Method of Manufacture", Ser. No. 278,913, filed June 29, 1981, now abandoned.

The efficiency of a flow-through filter in separating plasma from whole blood depends on the hematocrit of the donor, and the flow rate and pressure of the whole blood as it is pumped through the filter. Insufficient flow rates or whole blood pressure results in less than optimum yields. Excessive flow rates or whole blood pressures results in hemolysis, or damage to the red blood cells within the filter, and possible failure of the filter to exclude red cells from the collected plasma. Thus, a practical limit exists for the percentage of plasma that can be recovered by a flow-through membrane filter in a single pass of whole blood.

To improve the efficiency of blood fractionation systems it has been proposed that once-filtered whole blood be recirculated through the filter. This enables the filter to refilter previously-filtered whole blood, recovering an additional percentage of the remaining plasma component. A blood fractionation system providing such recirculation is shown in the copending application of Arnold C. Bilstad et al, entitled "Increased Yield Blood Component Collection System and Methods", Ser. No. 411,057, filed Aug. 24, 1982.

However, in certain procedures, as where a high hematocrit is encountered in whole blood drawn from a donor, the hematocrit of the once-filtered whole blood may be so high as to require a reduction in the filter rate and pressure with an attendant reduction in filter efficiency, to avoid hemolysis in the second pass. Furthermore, for user comfort it is desirable that in vivo blood fractionation systems withdraw whole blood from and return whole blood to the donor through a single phlebotomy needle at a single injection site. This necessitates either the use of a single dual-lumen phlebotomy needle, in conjunction with a continuous flow non-batch system, such as described in the copending application of Arnold C. Bilstad et al, entitled "Blood Fractionation Apparatus", Ser. No. 330,989, filed Dec. 15, 1981, or of a single-lumen phlebotomy needle in conjunction with a bidirectional batch system, whereby batches of whole blood are alternately drawn through the needle, passed through a plasma separation filter, and returned through the same needle. Such bidirectional single-lumen batch systems have the advantage of utilizing a smaller and potentially less traumatic single lumen needle.

A preferred single lumen batch-type blood fractionation system which provides operator-controlled partial recirculation during return cycles to reduce processing time and accommodate variations in the hematocrit of the processed whole blood is described in the copending application of Arnold C. Bilstad et al, entitled "Single Needle Blood Fractionation System Having Adjustable Recirculation Through Filter."

Basically, this system provides for user-controllable recirculation of whole blood through the system filter, thereby maintaining filter operating efficiency notwithstanding variations in whole blood hematocrit. Whole blood is drawn from the donor through a phlebotomy needle and associated bidirectional donor conduit and pumped through the system filter to a reservoir by an inlet pump. Upon the volume of fluid in the reservoir reaching a predetermined level, plasma-deficient whole blood is pumped from the reservoir to the donor conduit by a return pump, which operates at a higher rate than the inlet pump. By reason of the higher rate of the return pump flow is reversed in the donor conduit and processed whole blood is returned to the donor through the phlebotomy needle, without the need for valves for controlling fluid flow in the system. By controlling the relative speeds of the inlet and return pumps during the draw and return cycles, the percentage of recirculation can be varied to maintain a desired hematocrit at the filter.

To minimize inconvenience to the donor it is desirable that whole blood be withdrawn, processed and returned at as high a rate as possible. The use of a pressure cuff for improving the draw rate in a batch-type system, installed at a location above the system phlebotomy needle, and actuated during draw cycles and terminated in response to the weight of collected plasma corresponding to a completed batch, is shown in U.S. Pat. No. 4,086,924. However, no provision is made in this reference for controlling the pressure cuff in response to the volume of processed fluid in an intermediate reservoir.

A blood fractionation system incorporating a pressure cuff and control system responsive to the weight of an intermediate fluid reservoir is shown in the copending application of Arnold C. Bilstad et al, "Single Needle Blood Fractionation System Having Pressure Cuff Draw Mode Enhancement". The present invention is directed to a pressure cuff draw mode enhancement system and method operable with this fractionation system, wherein a pressure cuff is automatically pressurized upon the volume of filtered whole blood in an intermediate reservoir reaching a predetermined maximum level, and depressurized upon the volume in the reservoir falling below a predetermined minimum level, in conjunction with the operation of a return pump connected to return and/or recirculate the filtered whole blood.

Accordingly, it is a general object of the present invention to provide a new and improved pressure cuff draw mode enhancement system.

SUMMARY OF THE INVENTION

Accordingly, the invention is directed to a pressure cuff draw mode assist system and method for a blood fraction system of the type having a phlebotomy needle, flow-through separation means for separating plasma from whole blood, and an intermediate fluid storage reservoir. In one form, an inlet pump pumps whole blood from the phlebotomy needle through the separation means to the intermediate storage reservoir. A return pump pumps plasma-deficient whole blood from the reservoir to the phlebotomy needle. System control means responsive to the volume of fluid in the intermediate storage reservoir initiate operation of the return pump and pressurize the pressure cuff upon the filtered fluid reaching a predetermined maximum volume in the reservoir, and terminate operation of the pump and depressurize the pressure cuff upon the fluid in the reservoir reaching a predetermined minimum volume. By reason of the rate of the return pump being greater than the rate of the inlet pump, upon operation of the return pump a portion of the output of the reservoir dependent on the ratio of the pump rates is caused to flow through the inlet pump to the separation means, and the remaining portion of the output of the reservoir is caused to flow through the donor interface conduit. A cuff control circuit responsive to the actuating pressure level in the cuff prevents operation of the return pump until the actuating pressure has fallen below a predetermined level.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 9a is a simplified flow diagram of the blood fractionation system showing the system during a draw cycle.

FIG. 9b is a flow diagram similar to FIG. 9a showing the system in a return cycle.

FIG. 10 is a simplified depiction of certain operating parameters of the blood fractionation system useful in understanding the operation of the system.

FIG. 11 is a simplified depiction of the plasma collection characteristics of various types of blood fractionation systems.

DESCRIPTION OF THE PREFERRED EMBODIMENTS

Figure 1:
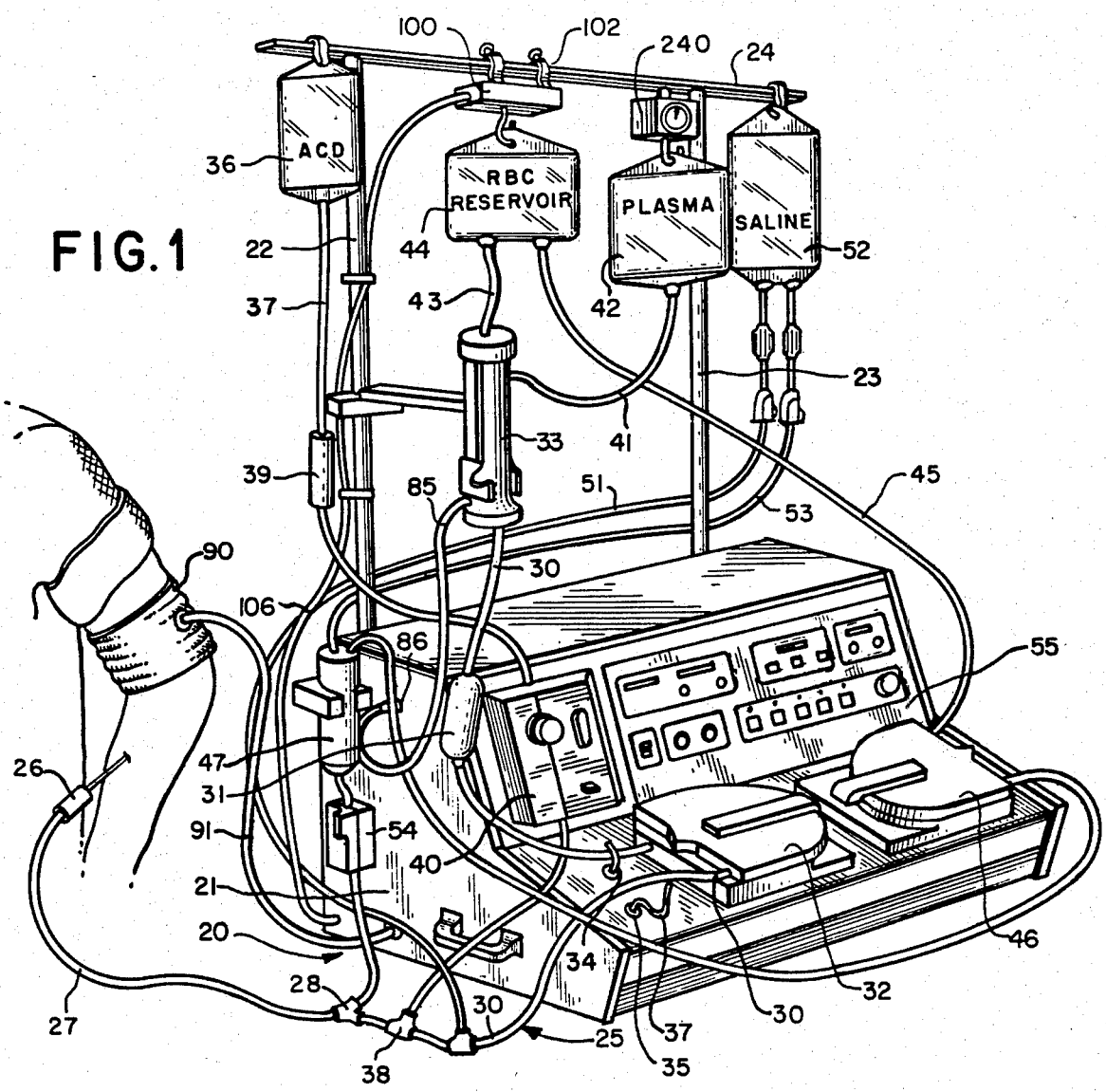
FIG. 1 is a perspective view of a single needle partial-recirculation filter-type blood fractionation apparatus having a pressure cuff draw mode enhancement system in accordance with the invention.

Referring to the Figures, and particularly to FIG. 1, a blood fractionation apparatus 20 for use in conjunction with a single needle filter-type plasma separation system having a filter recirculation and a pressure cuff assist system in accordance with the invention is incorporated within a table-mounted housing 21. The housing preferably includes a pair of vertical support poles 22 and 23 from which horizontal bar 24 is mounted to allow a plurality of collection and dispensing containers of conventional construction to be hung by means of appropriate hangers.

Figure 2:
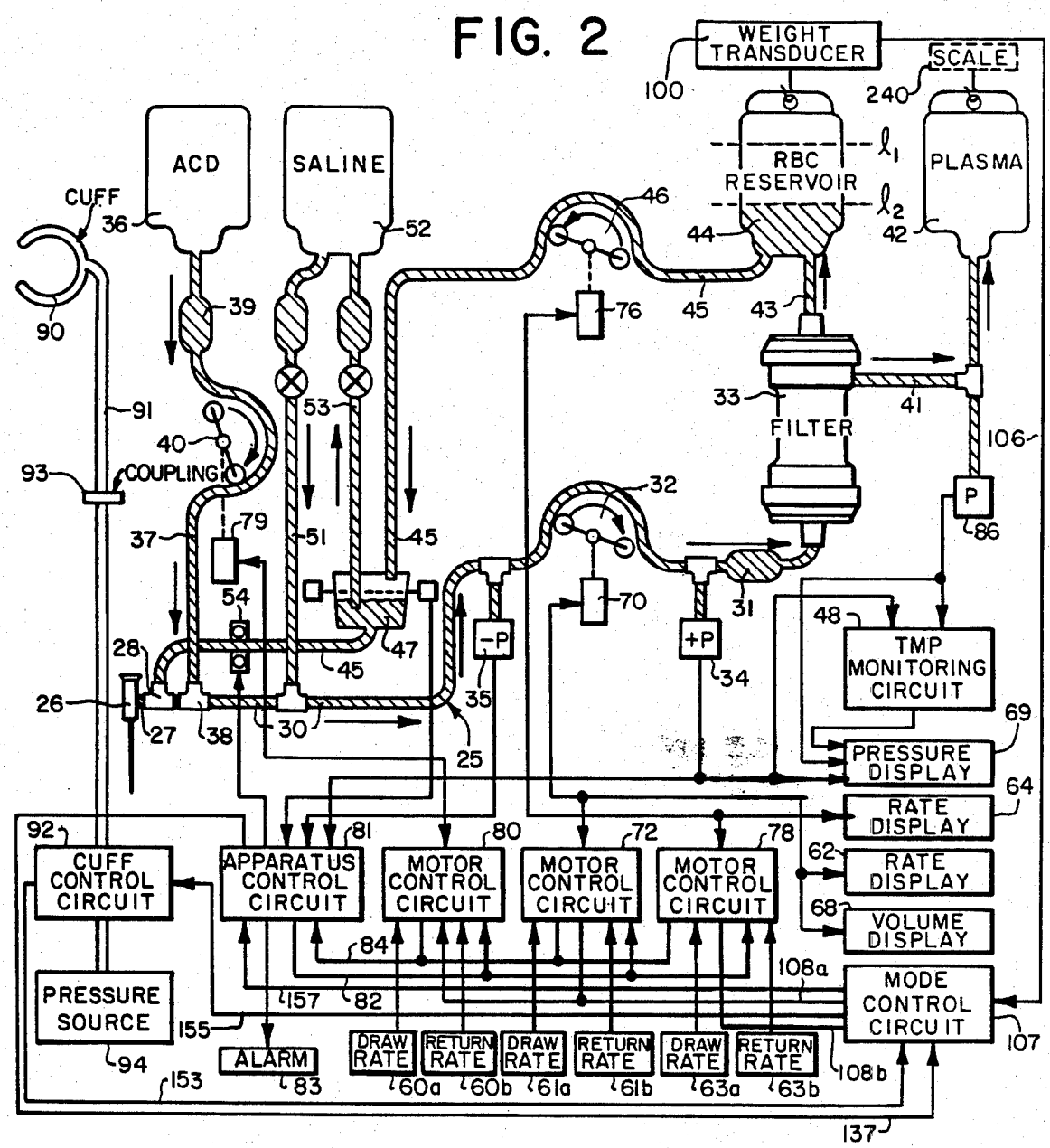
FIG. 2 is a functional block diagram showing the principal components of the blood fractionation apparatus and pressure cuff assist system of FIG. 1.

The blood fractionation apparatus 20 operates in conjunction with a disposable fluid circuit, generally identified by the reference numeral 25 in FIG. 1, and shown schematically in FIG. 2. The fluid circuit 25 includes a plurality of flexible plastic tubing segments which form fluid conduits between various components of the fluid circuit.

As shown in FIG. 2, whole blood derived from or returned to a donor is conveyed through the lumen of a single single-lumen phlebotomy needle 26 and a bidirectional donor interface conduit segment 27 to which the needle is connected. Conduit 27 communicates with a T-connector 28, which communicates with a tubing segment 30. Whole blood is conveyed through tubing segment 30 and an inline mixing chamber 31 by a peristaltic-type inlet pump 32 to a hollow fiber-type flow-through filter 33. The operation of the inlet pump is monitored by a positive pressure (+P) monitor circuit 34 connected to tubing segment 30 by a short tubing segment. Negative pressure, such as might occur upon the collapse of a vein, is monitored by means of a negative pressure (−P) monitor circuit 35 connected to tubing segment 30 upline of inlet pump 32 by another short tubing segment.

To prevent blood from clotting while in process anticoagulant (ACD) solution from a supply container 36 is introduced into conduit segment 30 through a tubing segment 37 and a T-connector 38. A drip chamber 39 may be provided inline in segment 37 to monitor ACD flow. A peristaltic-type pump 40 is provided along tubing segment 37 to provide a controlled rate of addition of the anticoagulant fluid to the whole blood.

Plasma separated from whole blood within filter 33 is conveyed by a tubing segment 41 to a plasma collection container 42. The pressure provided by inlet pump 32 provides flow through filter 33 to the collection container. A weight scale of conventional construction may be provided to provide an indication to the user of the volume of plasma collected.

Plasma-deficient blood from filter 33 is conveyed through a tubing segment 43 to an in-process fluid storage reservoir 44. In accordance with the invention, this plasma-deficient blood is periodically withdrawn from reservoir 44 through a tubing segment 45 by a peristaltic-type return pump 46 for return to conduit 27 at T-connector 28. The whole blood conveyed through tubing segment 45 passes through a combined bubble trap and fluid absence detector 47, which may be similar in structure and operation to that described in U.S. Pat. No. 4,341,116 to Arnold C. Bilstad et al.

Reservoir 44 and plasma container 42 are preferably hung at the same height to avoid the need for an equalizer valve at the whole blood and collected plasma outlets of filter 33. However, under other circumstances an equalizer valve may be provided to restrict the plasma outlet port until the pressure of the plasma in the filter reaches that of plasma-deficient blood flowing from the filter, and thereafter to modulate plasma flow through line 41 to maintain the pressure equivalence. A preferred construction for such an equalizer valve is described in the copending application of Clinton Kopp et al; "Membrane Plasmapheresis Apparatus and Procedure", Ser. No. 277,428; "Fluid Flow Control Device", Ser. No. 277,449; and "Fluid Flow Control Device", Ser. No. 277,414; filed June 25, 1981 and assigned to the present assignee. A transmembrane pressure (TMP) monitoring system 48, which may be as described in the copending application of Arnold C. Bilstad et al, "Trans-Membrane Pressure Monitoring System", Ser. No. 403,362, filed July 30, 1982, may be provided in apparatus 20 to assist the user in making adjustments for maximum operating efficiency of filter 33.

For system priming purposes, a saline fluid may be added to segment 30 through a tubing segment 51, which is connected at one end to a saline container 52 and at its other end to a T-connector in conduit segment 30. A second saline line 53 is provided between containers 52 and bubble trap 47 for use in the purging procedure. Drip chambers and clamps of conventional construction may be provided in lines 51 and 53 to assist the procedure. A safety clamp 54 positioned along tubing segment 45 downline of bubble trap 47 actuates in the event of detection of a bubble or in the event of a malfunction in the apparatus to preclude uncontrolled infusion of fluid into the donor.

Figure 3:
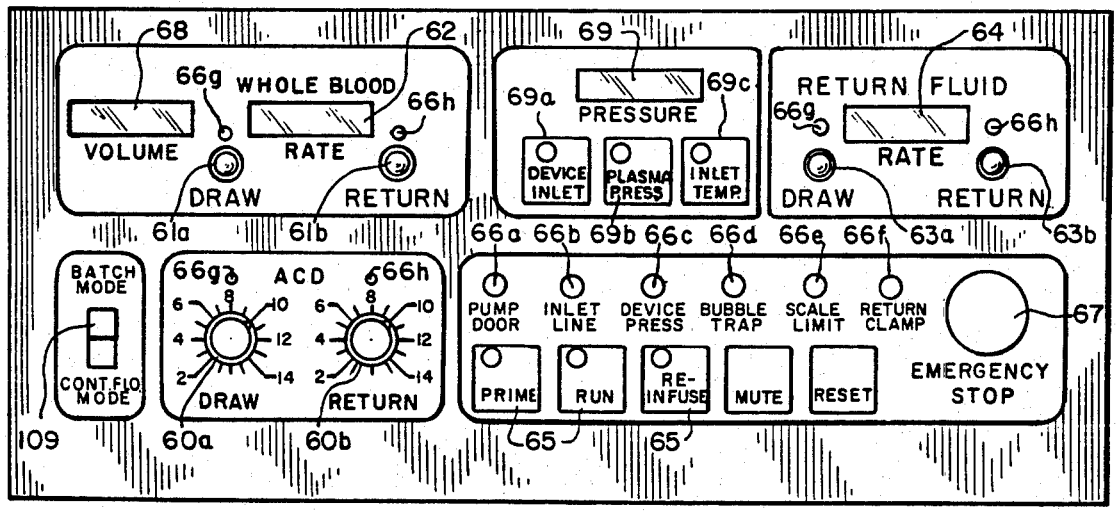
FIG. 3 is an enlarged front elevational view of the control panel of the blood fractionation apparatus of FIG. 1.

Referring to FIG. 1, the blood fractionation apparatus 20 includes a sloped control panel 55 containing operator-actuated controls for operating the apparatus. As shown in FIG. 3, control panel 55 includes a pair of selector switches 60a and 60b by which the draw and return mode operating speeds of anticoagulant pump 40 are set, a pair of potentiometer controls 61a and 61b and a digital readout 62 by which the draw and return mode operating speeds of the inlet pump 32 are controlled, and a pair of potentiometer controls 63a and 63b and a digital readout 64 by which the draw and return mode operating speeds of the return pump 46 are controlled. A plurality of push button switches are provided to establish the operator mode of the apparatus. A plurality of status indicating lights 66a–66f provide status and alarm indications, and three pairs of indicator lights 66g and 66h associated with respective ones of the system pumps indicate the draw and return operating cycles of the pumps. An emergency stop switch 67 provides for an immediate operator-initiated shutdown in the event of a malfunction.

A display 68 displays the total volume of whole blood processed by the apparatus since the beginning of a particular procedure. A display 69 displays fluid pressure readings, as called for by a trio of pushbutton switches 69a–69c. Actuation of switch 69a causes the inlet pressure of filter 33 to be displayed. Actuation of switch 69b causes the collected plasma pressure of the filter to be displayed. Actuation of switch 69c causes the inlet transmembrane pressure (TMP) of the iflter to be displayed as derived by TMP monitoring circuit 48.

Referring to FIG. 2, the inlet pump 32 is driven by a motor 70. Power for operating motor 70 is provided by a motor control circuit 72 which responds to potentiometer controls 61a and 61b and a tachometer feedback signal from a tachometer (not shown in FIG. 2) associated with the motor to maintain a desired motor operating speed. The inlet pump flow rate is displayed by readout 62 as part of a display circuit which responds to the tachometer output signal.

Similarly, the return pump 46 is driven by a motor 76. Power for motor 76 is provided by a motor control circuit 78 which responds to a tachometer feedback signal from a tachometer (not shown in FIG. 2) associated with the motor and panel-mounted potentiometers 63a and 63b to maintain a desired constant motor speed. The return pump flow rate is displayed by readout 64 as part of the display circuit.

The anticoagulant pump 40 is driven by a stepper motor 79. Drive signals for motor 79 are developed by a motor control circuit 80 which responds to rate selection switches 60a and 60b to maintain a desired anticoagulant flow rate.

The operation of the various pump motors is controlled by a control circuit 81 which includes the mode select pushbutton switches 65 on control panel 55. System malfunctions, such as negative pressure at pressure monitor 35, or excessive positive pressure at pressure monitor 34, or the occurrence of a bubble or other fluid absence as signaled at the output of the combined bubble trap and fluid absence detector 47, result in the application of an alarm signal to control circuit 81. This circuit in turn produces a control signal which is applied to motor control circuits 72, 78 and 80 by way of a motor control line 82 to interrupt operation of the motors. In addition, an alarm 83 associated with the control circuit may be sounded and an appropriate one of indicator lamps 66a–66f may be lit to alert the operator. Each of motor control circuits 72, 78 and 80 also includes internal stall protection where an alarm signal is developed and applied to control circuit 81 by way of a control line 84 to terminate operation of blood fractionation apparatus 20 in the event of a pump malfunction.

To provide for increased draw rates, the single needle controlled-recirculation blood fractionation system 20 includes, in accordance with the invention, a pressure cuff 90 adapted for operative association with the limb of the donor adjacent to the injection site. The pressure cuff, which may be conventional in construction, is connected to housing 21 by a tubing segment 91. This segment conveys operating pressure to the cuff as provided by a cuff control circuit 92 within the blood fractionation apparatus. A coupling 93 may be provided in the tubing to facilitate disconnecting the pressure cuff from the apparatus when the cuff is not in use. Necessary operating pressure for the pressure cuff is preferably provided by a pressure source 94 within the housing, although an external source can be used instead.

In performing a normal batch-mode procedure blood fraction apparatus 20 operates in alternate draw and return cycles. During each draw cycle inlet pump 32 operates to draw whole blood through the phlebotomy needle into conduit 27 and to advance the whole blood through tubing 30 and mixing chamber 31 to filter 33. Afte a predetermined volume of plasma-deficient whole blood has been pumped through filter 33 into reservoir 44, the draw cycle is terminated and the return cycle is initiated. Return pump 46 then operates to pump plasma-deficient blood from reservoir 44 into conduit 30 at T-fitting 28. Depending on the relative operating speed of return pump 46 and inlet pump 32, a user-selectable portion of deficient whole blood is pumped into mixing chamber 31 for subsequent recirculation through filter 33, and the remaining portion is returned to the donor through donor tubing segment 27 and needle 26. Upon the volume of the plasma-deficient blood in reservoir 44 reaching a predetermined minimum level, the return cycle is terminated and the draw cycle is again initiated. The cycles continue in alternation until a desired quantity of blood has been processed or a desired quantity of plasma has been collected.

Figure 4:
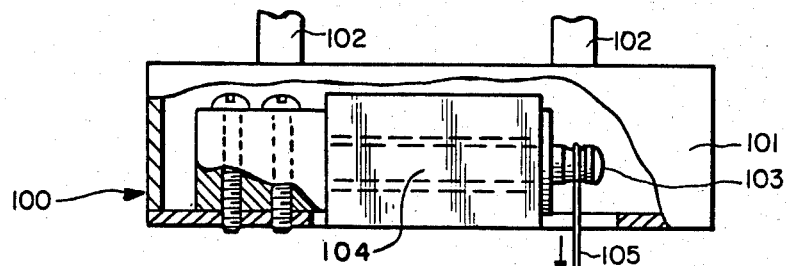
FIG. 4 is an enlarged front elevational view partially in section of an electrical weight transducer and intermediate fluid storage container utilized in the blood fractionation apparatus.

The blood fractionation apparatus 20 is conditioned between its draw and return cycles by a circuit responsive to the weight of the intermediate in-process fluid reservoir 44. To this end, the blood fractionation apparatus 20 includes a weight transducer unit 100 from which the reservoir container 44 is suspended. As shown in FIG. 4, the weight transducer unit 100 may include a housing 101 mounted by clamps 102 or other appropriate means to the horizontal support bar 24 of the apparatus. Within housing 101 reservoir 44 is suspended from the sense pin 103 of an electrical weight transducer 104 by a wire clip 105 or other appropriate means. Weight transducer 104, which may be conventional in construction and operation, provides an electrical output signal which is conveyed to the apparatus housing 21 through a connecting cable 106.

Within housing 21, blood fractionation apparatus 20 includes a mode control circuit 107 (FIG. 2) which provides in accordance with the magnitude of the signal from weight transducer 100, a mode control signal for application to motor control circuits 72, 78 and 80 by way of a control line 108. A mode select switch 109, located on control panel 55 (FIG. 3), is provided to enable the user to selectively disable mode control circuit 107 when it is desired to operate the plasmapheresis apparatus as a continuously running system, as in conjunction with a continuous-flow two needle in vivo blood fractionation procedure.

Figure 5:
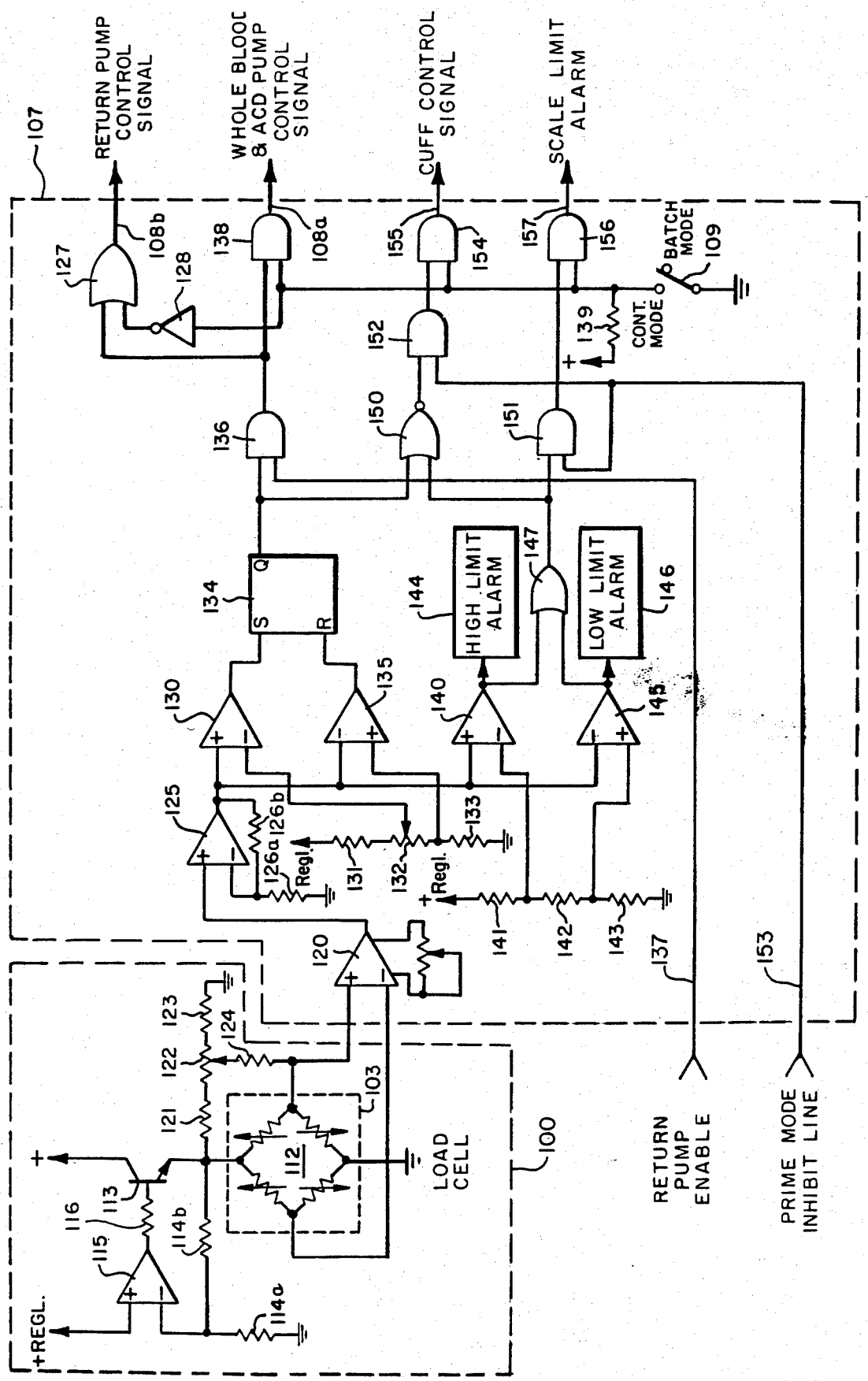
FIG. 5 is a simplified schematic diagram of the mode control circuit utilized in the blood fractionation apparatus.

Referring to FIG. 5, within the weight transducer unit 100 the weight transducer 104 is seen to comprise a strain gauge bridge circuit 112. One input terminal of network 112 is connected to a source of positive current through a series-connected transistor 113, and the other input terminal is connected to ground. The conduction level of transistor 113, and hence the voltage applied to network 112, is controlled by a differential amplifier 115 having its non-inverting input connected to a source of regulated voltage, and its inverting input connected to a voltage divider comprising a pair of resistors 114a and 114b. The output of differential amplifier 115 is connected to the base of transistor 113 through a resistor 116 with the result that the voltage applied to network 112 is held constant at all times.

The output of bridge circuit 112, which depends on the force exerted on sense pin 103, is applied to the inputs of a differential amplifier 120 included in mode control circuit 107. A necessary offset is introduced to this signal by an adjustable voltage divider network comprising resistors 121, 122, 123 and 124 connected between the regulated input terminal of bridge 112 and ground and the non-inverting input of differential amplifier 120. The output of amplifier 120 is applied to the non-inverting input of a differential amplifier 125 for further amplification. A pair of resistors 126a and 126b form a conventional degenerative gain stabilizing network.

To establish a minimum volume level for the fluid in reservoir 44 the output of amplifier 125 is applied to the non-inverting input of a comparator amplifier 130. The inverting input of this amplifier is connected to a voltage divider comprising a resistor 131, a potentiometer 132 and a resistor 133 connected between a source of regulated voltage and ground. Depending on the setting of potentiometer 132, differential amplifier 130 produces an output signal as the volume of whole blood reaches a predetermined level within reservoir 44. This output signal is applied to the set input of an RS-type flip flop 134 which provides at its Q output the draw and return cycle mode control signal.

The output of differential amplifier 125 is also applied to the inverting input of a differential amplifier 135 to establish a minimum volume level at which the return cycle will be terminated and the draw cycle will be initiated. To this end, the non-inverting input of differential amplifier 135 receives a reference voltage developed at the juncture of potentiometer 132 and resistor 133 which establishes the threshold of comparator amplifier 135 at the minimum level. The output of amplifier 135 is applied to the reset input of RS flip-flop 134 to reset that device upon the reservoir being emptied to the minimum level.

The Q output of RS flip-flop 134 is connected to one input of an and gate 136. The other input of this gate is connected to return pump enable line 137. In the presence of enabling signals on line 137, AND gate 136 conveys the Q output of flip-flop 134 to one input of an AND gate 138 and to one input of an OR gate 127. The other input of gate 138 is connected through mode select switch 109 to ground, and by a resistor 139 to a positive current source. OR gate 127 is similarly connected through an inverter 128. Consequently, when the mode switch is open, i.e., set for batch-mode operation, AND gate 138 is enabled and OR gate 127 receives a continuous logic low signal, enabling that device relative to the Q output. Provided AND gate 138 and OR gate 127 are enabled, the Q output of flip-flop 134 is applied to pump control line 108a and 108b. Control line 108a conditions the ACD and inlet pump between draw and return cycles. Control line 108b conditions the return pump motor control circuits between draw and return modes.

To establish an over-volume alarm for reservoir 44, the weight-indicative analog signal from amplifier 125 is also applied to the non-inverting input of a comparator amplifier 140. The inverting input of this amplifier is connected to a voltage divider comprising resistors 141–143 connected between positive current source and ground. This establishes a threshold for the output signal of amplifier 125 above which comparator 140 provides an output signal. This signal is applied to a high limit alarm 144, which may be of conventional construction to provide visual and aural alarm indications.

To establish an under-volume alarm for reservoir 44, the weight signal from amplifier 125 is applied to the inverting input of a comparator amplifier 145. The non-inverting input of this amplifier is connected to the juncture of resistor 142 and 143 to establish a threshold level below which comparator 145 will produce an output signal. This signal is applied to a low limit alarm 146, which may be of conventional construction to provide visual and aural alarm indications.

The outputs of comparator amplifiers 140 and 145 are also connected to respective inputs of an OR gate 147, which provides an output in the event of either alarm. The output of this gate is connected to one input of an AND gate 151 and to one input of a NOR gate 150. In the absence of outputs from OR gate 147 and RS flip-flop 134, NOR gate 150 provides an output which is applied to one input of an AND gate 152. The remaining input of this gate is connected to the apparatus control circuit 81 by a prime mode inhibit line 153. When the apparatus is operating in the prime mode, a signal is present on this line which inhibits AND gate 152 The output of AND gate 152, which comprises a cuff control signal, is applied to one input of an AND gate 154, which is enabled only when switch 109 is set for recirculation. The output of AND gate 154 is applied to the pressure cuff control circuit 92 by way of a cuff control line 155.

The prime mode inhibit signal on line 153 is also applied to the remaining input of AND gate 151. In the absence of the inhibit signal, AND gate 151 produces an output signal upon the occurrence of either a high limit alarm or a low limit alarm. This output signal is applied through an AND gate 156 to apparatus control circuit 81 by way of alarm control line 157 to terminate operation of the blood fractionation apparatus.

When mode switch 109 is closed, indicating operator selection of a continuous-run mode, AND gates 138, 154 and 156 are inhibited and no control signals can be provided by mode control circuit 107 to control lines 108a, 155 and 157. This causes the ACD and inlet pumps to remain under control of their respective draw rate control potentiometers 60a and 61a, and precludes the production of false cuff control and alarm signals upon movement or removal of the weight transducer. The return pump mode control line 108b is forced logic high at this time, causing the return pump to operate under the control of its return rate potentiometer 63b. This allows the draw rate potentiometer 63a to be omitted in those applications where the return pump is always inoperative during the draw mode.

Figure 6:
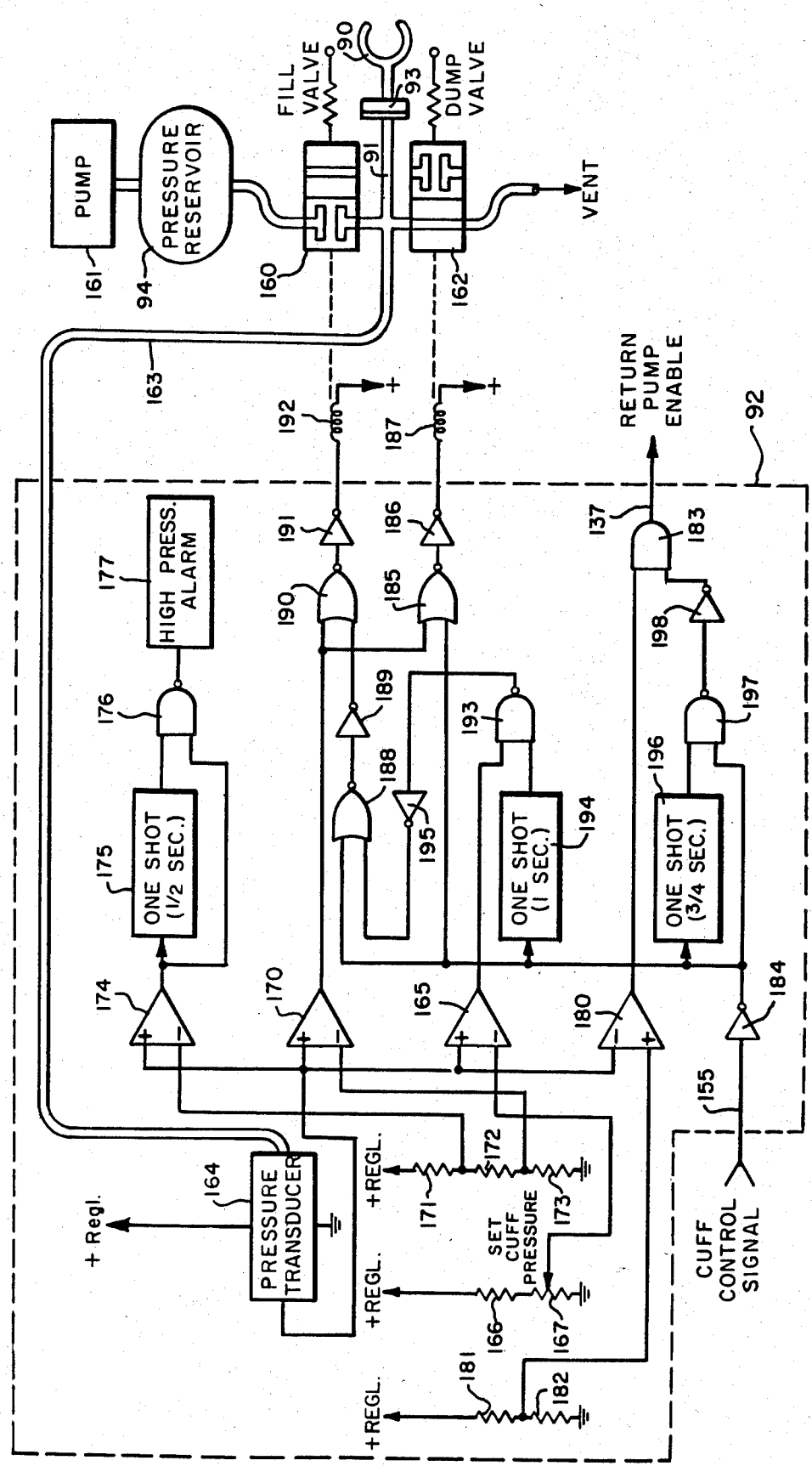
FIG. 6 is a simplified schematic diagram of the pressure cuff control circuit of the blood fractionation apparatus.

Pressure cuff 90 is pressurized during each draw cycle cuff control circuit 92. Referring to FIG. 6, tubing segment 91 is connected by a normally-closed electrically-actuated fill valve 160 to reservoir 94 and pump 161. Upon actuation of valve 160, pressure from reservoir is supplied to cuff 90, causing the cuff to compress the donor's arm to assist in blood withdrawal.

Pressure cuff 90 is depressurized during each return cycle by a normally-open electrically-actuated dump valve 162. When this valve is not actuated, pressure is vented from cuff 90 and the cuff has no effect on the donor. By reason of valve 160 being normally closed and valve 162 being normally open, a failsafe control arrangement is provided whereby the cuff is depressurized in the event of a power failure or other malfunction.

To provide for maintaining a uniform predetermined operating pressure at pressure cuff 90, the cuff supply line is connected by a tubing segment 163 to a pressure transducer 164 within cuff control circuit 92. Transducer 164, which may be conventional in construction and operation, is supplied by a regulated voltage source and produces an analog output signal indicative of the pressure present in the cuff. This signal is applied to the non-inverting input of a comparator 165, which serves to establish the nominal operating pressure of the cuff. The inverting input of comparator 165 is connected to a voltage divider comprising a resistor 166 and a potentiometer 167, which establishes a threshold voltage corresponding to the nominal pressure above which an output signal is produced by the comparator.

The pressure-indicative transducer signal is also applied to the non-inverting input of a comparator amplifier 170, which establishes a maximum operating pressure above which pressure will be dumped from the cuff. The inverting input of comparator 170 is connected to a voltage divider comprising resistors 171–173, which applies a reference voltage to the input corresponding to the dump limit. In the event that the dump level is exceeded, as in the event of a malfunction, a comparator amplifier 174 is biased by the voltage divider to provide an output upon effecting a comparison with the transducer output signal. This signal is applied through a one-shot flip-flop 175 and a NAND gate 176, which provide a short delay, to a high pressure aural and visual alarm 177 of conventional construction.

A further comparison, indicating that cuff pressure has fallen to a level where whole blood can be returned to the donor, is provided by a comparator amplifier 180. The transducer output signal is applied to the inverting input of this comparator, and a reference voltage is applied to the non-inverting input by a voltage divider comprising a pair of resistors 181 and 182. Upon the cuff pressure falling below the minimum threshold level set by comparator 180, the comparator produces an output signal which is applied through an AND gate 183 to the return pump enable control line 137.

In operation, mode control circuit 107 produces a cuff control signal upon the volume of plasma-deficient whole blood in reservoir 44 reaching a predetermined level. Assuming mode switch 109 is set for recirculation mode operation, the cuff control signal is applied by control line 155 to cuff control circuit 92. There, after inversion in an inverter 184, the control signal is applied to one input of a NOR gate 185. The output of this gate is applied through an inverter 186 to the solenoid 187 of dump valve 162, causing the dump valve to be actuated closed in the presence of a cuff control signal on line 155.

At the same time, the inverted cuff control signal is applied through a NOR gate 188, an inverter 189, a NOR gate 190 and an inverter 191 to the solenoid 192 of fill valve 160, causing that valve to open. Since fill valve 160 is now open and dump valve 162 is now closed, the pressure applied to pressure cuff 90 increases. As the pressure increases, the output signal developed by transducer 164 increases.

When the transducer signal reaches the nominal level established by comparator amplifier 165, this comparator provides an output signal to one input of a NAND gate 193. The other input of this gate receives the output of a one-shot flip-flop 194, which in accordance with one aspect of the invention, triggers in response to the occurrence of a cuff control signal on line 155 to inhibit the gate for a short time interval following each actuation of the cuff. This prevents pressure transients, which occur during the initial pressurization of the pressure cuff at the beginning of each draw cycle, and which may cause comparator 165 to produce an output, from closing the fill valve and thereby slowing the initial pressurization process. After this delay period, the nominal pressure signal is applied through an inverter 195 to the remaining input of NOR gate 188, where it serves to de-energize solenoid 192 and hence close fill valve 160. Thus after the initial delay period established by flip-flop 194, when the nominal pressure level is reached, the supply valve is closed, and the cuff pressure is maintained at the predetermined nominal level.

The inverted cuff control signal is also applied to a one-shot flip-flop 196 and a NAND gate 197. These components together provide an output signal through an inverter 198 to AND gate 183 which inhibits the AND gate for a predetermined latch period of the one-shot flip-flop 196 following termination of the inverted pressure cuff control signal. This, in accordance with another aspect of the invention, prevents the return pump from operating until a predetermined delay period has passed, notwithstanding the sensed pressure level in the cuff having earlier fallen below the minimum threshold level.

Figure 7A:
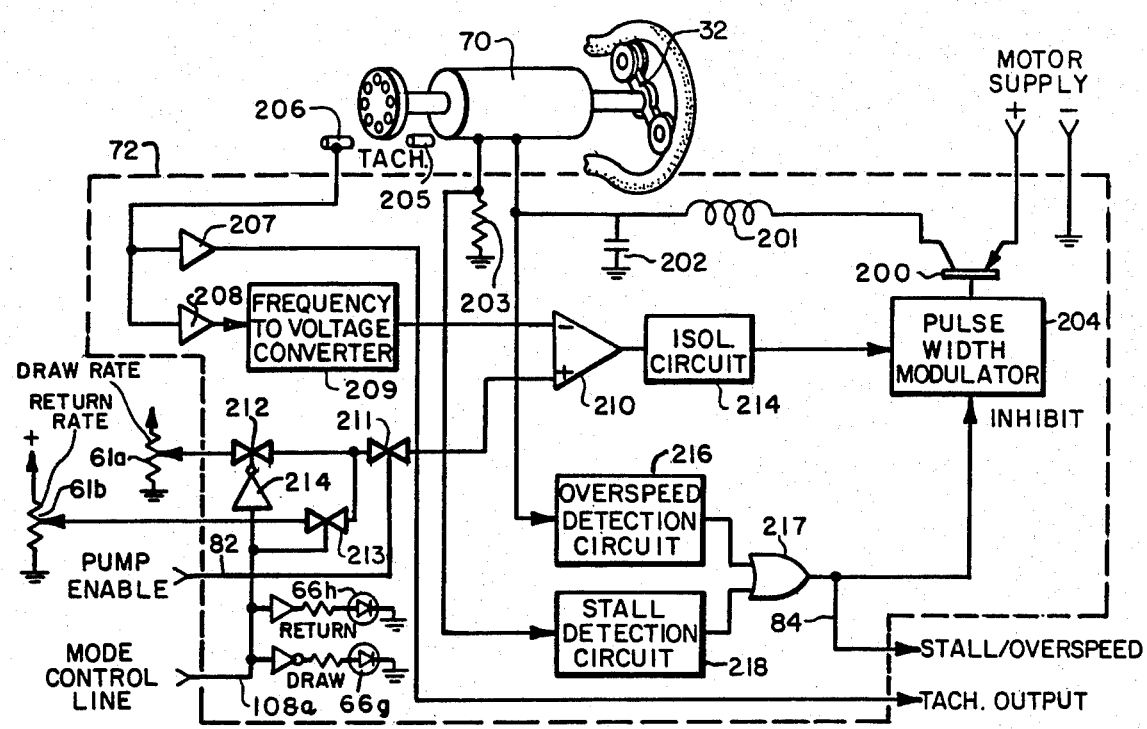
FIG. 7a is a simplified schematic diagram of the inlet pump motor control circuits of the blood fractionation apparatus.

Referring to FIG. 7a, the motor control circuit 72 provided for supplying operating power to the inlet pump motor 70 comprises a series-connected power transistor 200 and a reactance control network comprising an inductance 201 and a capacitor 202. These components supply power from a unidirectional motor current source (not shown) to the motor. The return line from the motor includes a series-connected current metering resistor 203.

Pump motor 70 is a direct current type motor and receives excitation over a variable duty cycle through power transistor 200. Conduction of this transistor is controlled by a pulse width modulator 204 which provides an appropriate control signal to the base electrode of the transistor. A tachometer formed by a light emitting diode 205 and a photodetector 206 operates in a conventional manner to provide output pulses indicative of incremental rotation of the pump motor. These pulses are applied to a tachometer output line through an amplifier 207 for use by other systems within the apparatus, and through an amplifier 208 to a frequency-to-voltage converter circuit 209. This circuit develops an analog output voltage in proportion to the frequency of the tachometer pulses. This signal is applied to the inverting input of a comparator amplifier 210, wherein it is compared with a speed control signal applied to the noninverting input from potentiometer 61a or 61b through a trio of analog devices 211–213.

The control gate of switch device 211 is connected to the pump control line 82 so that in the absence of an appropriate motor enabling signal from the apparatus control circuit 81 no reference signal is applied to comparator 210. The control gate of switch device 212 is connected to mode control line 108a through an inverter 214 so that in the absence of a logic high signal on this control line an analog control signal may be applied to comparator 210 by the draw mode whole blood rate control potentiometer 61a. The control gate of switch device 213 is connected directly to mode control line 108, so that in the presence of a logic high signal on this line the output of the return rate potentiometer 61b is applied to comparator 210.

Comparator amplifier 210 operates in a conventional manner to produce an output signal indicative of the difference between its inputs. This output signal is applied through an isolation circuit 214 to pulse-width modulator 204, wherein it controls the duty cycle of power transistor 200, and hence the speed of pump motor 70.

To provide protection against overspeed operation, the excitation level applied to pump motor 70 is continuously monitored by an overspeed detection circuit 216. In the event of an overspeed condition, this circuit provides an output which is coupled through an OR gate 217 to the alarm output line 84, and to the inhibit input of pulse width modulator 204, wherein it prevents the application of current to the base of transistor 200, thereby stopping the motor. Additional protection against malfunction is provided by a stall detection circuit 218 which provides an input to OR gate 217 upon motor 70 becoming stalled, as detected by the voltage level across series-connected resistor 203.

Figure 7B:
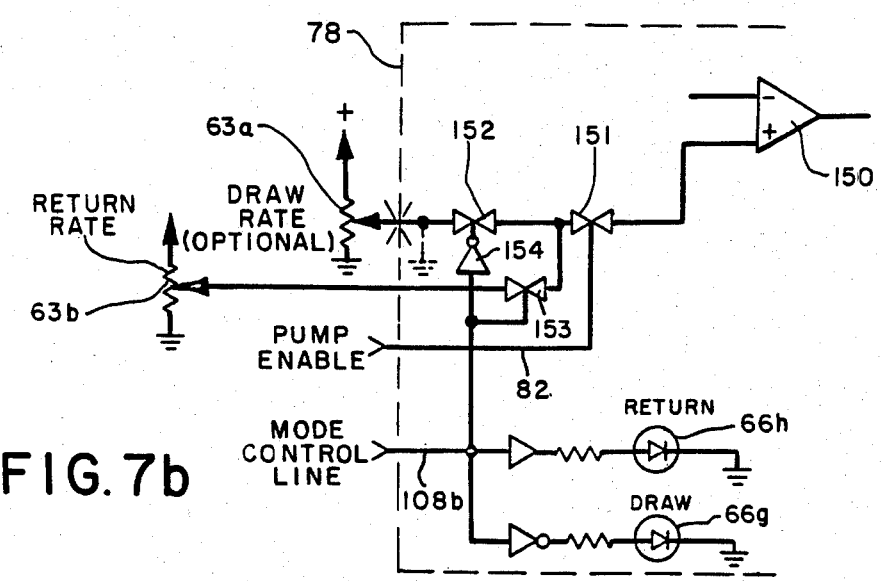
FIG. 7b is a simplified schematic diagram similar to FIG. 7a showing a portion of the return pump motor control circuit.

The return pump motor control circuit 78 may be identical to motor control circuit 72, except for control line 108b and rate controls 63a and 63b, as shown in FIG. 7b.

Figure 8:
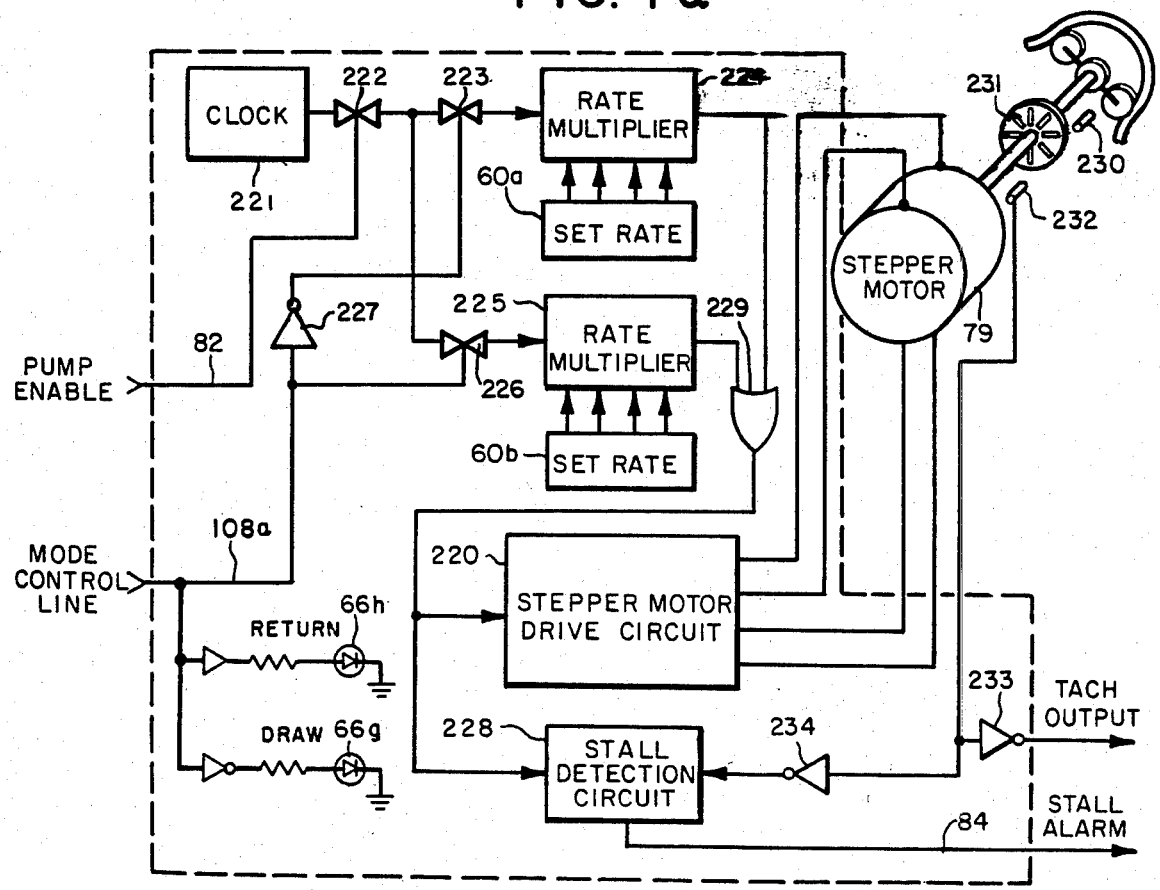
FIG. 8 is a simplified schematic diagram of the ACD pump motor control circuit of the blood fractionation apparatus.

Referring to FIG. 8, a multi-phase drive signal is applied to the anticoagulant pump stepper motor 79 by a stepper motor drive circuit 220 of conventional design. Control pulses for initiating the multi-phase drive signal from drive circuit 220, and consequently each incremental rotation of the motor, are provided by a clock circuit 221. In the draw mode, output pulses from the clock are applied through a pair of analog switch devices 222 and 223 to a rate multiplier 224. Rate multiplier 224, which may be conventional in construction and operation, responds to an operator-selected rate set by switch 60a to provide a preselected rate multiplication to the applied clock pulses. This results in stepper motor drive circuit 220 being impulsed at a user-selected rate, and consequently the stepper motor 79 being driven at the desired rate.

Alternatively, clock pulses from clock 221 are supplied to a second rate multiplier 225 through switch device 222 and a third analog switch device 226. When devices 222 and 226 are conductive, rate multiplier 225 is active to control motor speed according to the setting of return mode rate selector switch 60b.

Control over operation of stepper motor 79 is obtained by apparatus control circuit 81 by applying the pump enable control signal developed on control line 82 to analog switch device 222. During batch mode operation of the blood fractionation apparatus, analog switch device 222 is enabled, and switch device 223, which is connected to mode control line 108 through an inverter 227. is enabled during each draw cycle to render switch 60a operative. Switch device 226, which is connected directly to control line 108, is conductive only during each return cycle. Consequently, switch 60b controls return rate. In a continuous flow procedure, control line 108a provides a continuous logic low signal and only rate multiplier 224 and switch 60a are utilized. The outputs of rate multipliers 224 and 225 are applied to stepper motor drive circuit 220 and a stall detection circuit 228 through an OR gate 229.

The anticoagulant pump drive circuit 80 also includes a tachometer comprising a light emitting diode 230, a slotted disk 231 and a photodetector 232. As disk 231 turns with motor 79, output pulses produced by photodetector 232 are supplied through an inverter 233 to a tach output line. Pulses are also supplied through a second inverter amplifier 234 to stall detector 228, which provides an output on alarm line 84 upon stepper motor 79 stalling.

The batch mode operation of blood fractionation system 20 is illustrated in FIGS. 9a and 9b. During the draw cycle, as shown in FIG. 9a, pressure cuff 90 is pressurized and whole blood is drawn from a donor through the single-lumen phlebotomy needle 26 and the bidirectional donor interface conduit 27 by inlet pump 32, which pumps the whole blood along conduit segment 30 to mixing chamber 31. Within the mixing chamber, the freshly drawn whole blood is mixed with whole blood previously advanced along segment 30 by pump 32 and the resulting mixture is advanced through filter 33 to reservoir 44.

As the mixed whole blood from chamber 31 passes through filter 33, a portion of the plasma component contained therein is separated from the whole blood by the membrane element of the filter and is caused to flow through tubing segment 41 to plasma collection container 42. The volume of plasma thus collected can be readily determined by reference to a conventional weight scale 240 from which the plasma collection container is suspended Alternatively, a collected volume monitoring system such as that described in the copending application of Arnold C. Bilstad et al, entitled "Blood Fractionation Apparatus Having Collected Volume Monitoring System", Ser. No. 330,899, filed Dec. 15, 1981, may be utilized to provide a direct readout of collected plasma volume.

During the draw cycle the operating rate of the inlet pump 32 is set by potentiometer 61i a. The operating rate of the replacement pump 46, which is normally not operative during the draw cycle, may be set to zero by setting potentiometer 63a to zero. As an alternative, to preclude operation of the return pump 46 during the draw cycle, potentiometer 63a may be eliminated in the return pump motor control circuit 78 and the input to analog switch device 152 in that circuit may be connected to ground, as shown in FIG. 7b. The operating rate of ACD pump 40 is set by selector switch 60a to operate at a rate appropriate to the operating rate of inlet pump 32 to maintain a desired ratio of ACD to whole blood.

The plasma-deficient whole blood from the filter continues to collect in reservoir 44 during the draw cycle. As the weight of the whole blood in the reservoir increases, transducer 100 produces a progressively increasing output signal. When this signal reaches a level corresponding to fluid level $l_1$ in reservoir 44, the signal applied to comparator 130 (FIG. 5) by differential amplifier 125 causes comparator 130 to produce an output signal which conditions RS flip-flop 134 to its set state. As a consequence, the Q output of flip-flop 134 becomes logic high, and, assuming AND gate 138 is enabled by mode switch 109 being open for batch operation, mode control lines 108a and 108b convey logic high control signals. This causes termination of the draw cycle and initiation of the return cycle.

During the return cycle, as illustrated in FIG. 9b, the pressure cuff 90 is depressurized and return pump 46 is operated to pump plasma-deficient whole blood from reservoir 44 back through the combined bubble trap and fluid absence detector 47 and conduit segment 45 to donor conduit 27 and conduit segment 30 at T-connector 28. The flow rate of the plasma-deficient whole blood, as established by return pump 46 under the control of potentiometer 63b, is set higher than the flow rate of the whole blood in conduit segment 30, as established by inlet pump 32 under the control of potentiometer 60b. As a result, the plasma-deficient whole blood flowing from reservoir 44 is caused to divide between donor conduit 27, wherein it causes a flow reversal and flow into the donor through the lumen of the single-lumen phlebotomy needle, and conduit segment 30, wherein it is advanced toward mixing chamber 31 and filter 33.

Within mixing chamber 31 the recirculating portion of the plasma-deficient whole blood divided into conduit segment 30 is caused to mix with whole blood previously pumped into the chamber, as during the previous draw cycle of the system. The resulting mixture, which has a hematocrit determined by the hematocrits of the recirculating plasma-deficient whole blood and the previously pumped resident whole blood, is advanced through filter 33 into reservoir 44 by inlet pump 32. This causes an additional quantity of plasma to be separated from the whole blood mixture by filter 33 and stored in plasma container 42.

The ratio of plasma-deficient whole blood returned to the donor to plasma-deficient whole blood recirculated through filter 33 is dependent on the relative operating rates of the inlet pump 32 and the return pump 46. For a relatively higher return pump rate, a higher percentage of plasma-deficient whole blood is returned to the donor. The actual operating rates of the inlet and return pumps during the return cycle are set by the operator by means of potentiometers 61b and 63b on panel 55. In practice, these rates are limited by practical considerations, such as the flow rate and pressure requirements of filter 33, the maximum permissible draw and return rates of the donor, and the capacity of the conduit segments and associated system components. The ACD pump 40 may be operated during the return cycle at a rate selected by selector switch 60b to maintain a desired percentage of ACD solution in the in-process whole blood.

Operation in the return cycle continues until the volume of plasma-deficient whole blood in fluid reservoir 44 reaches a predetermined minimum level, corresponding to level $l_2$ in FIG. 9b. At this time the output signal produced by weight transducer 100 causes comparator 135 (FIG. 5) to toggle RS flip-flop 134 to its reset state, causing a logic low on mode control lines 108a and 108b. This causes analog switch devices 212 (FIG. 2) and 226 (FIG. 8) to close and analog switch devices 213 and 223 to open, thereby enabling the inlet pump draw cycle potentiometer 61a, the return pump draw cycle potentiometer 63a and the ACD draw cycle rate selector switch 60a. Consequently, the return cycle is terminated and a new draw cycle is initiated.

Referring to FIG. 10, during alternate draw and return cycles of blood fractionation system 20 the volume 241 of plasma-deficient blood in reservoir 44 is seen to vary between a predetermined maximum level, corresponding to level $1_1$, and a predetermined minimum level, corresponding to level $1_2$. At the same time, the volume 242 of plasma collected in container 42 is seen to increase with each cycle, at a faster rate during draw cycles as freshly drawn blood is filtered, and at a slower rate during return cycles, as recirculated blood is filtered with previously drawn blood. Normally, the fractionation procedure is continued until a desired volume of plasma (or other desired blood fraction) has been collected, as determined by the weight of the collected plasma as read on scale 240.

As a result of the partial recirculation of plasma-deficient whole blood from reservoir 44 during each return cycle, the system filter operates during both draw and return cycles and the time required for separating a given volume of plasma is significantly reduced. Pressurization of the cuff 90 during each draw cycle is illustrated by cuff pressure plot 243.

For hematocrits within the normally encountered range of 40-55% the pressure cuff-assisted single-lumen single needle partial-recirculation blood fractionation system of the present invention requires less processing time and less whole blood than a non-recirculation single-lumen single needle batch system wherein whole blood is drawn, filtered and returned in discrete batches and no recirculation through the filter takes place. Only the more complex and less convenient two needle continuous flow system has a greater system efficiency. This is illustrated in FIG. 11, wherein collected plasma volumes 244, 245 and 246 are depicted for two needle continuous, single needle recirculation and single needle batch systems, respectively.

Figure 12:
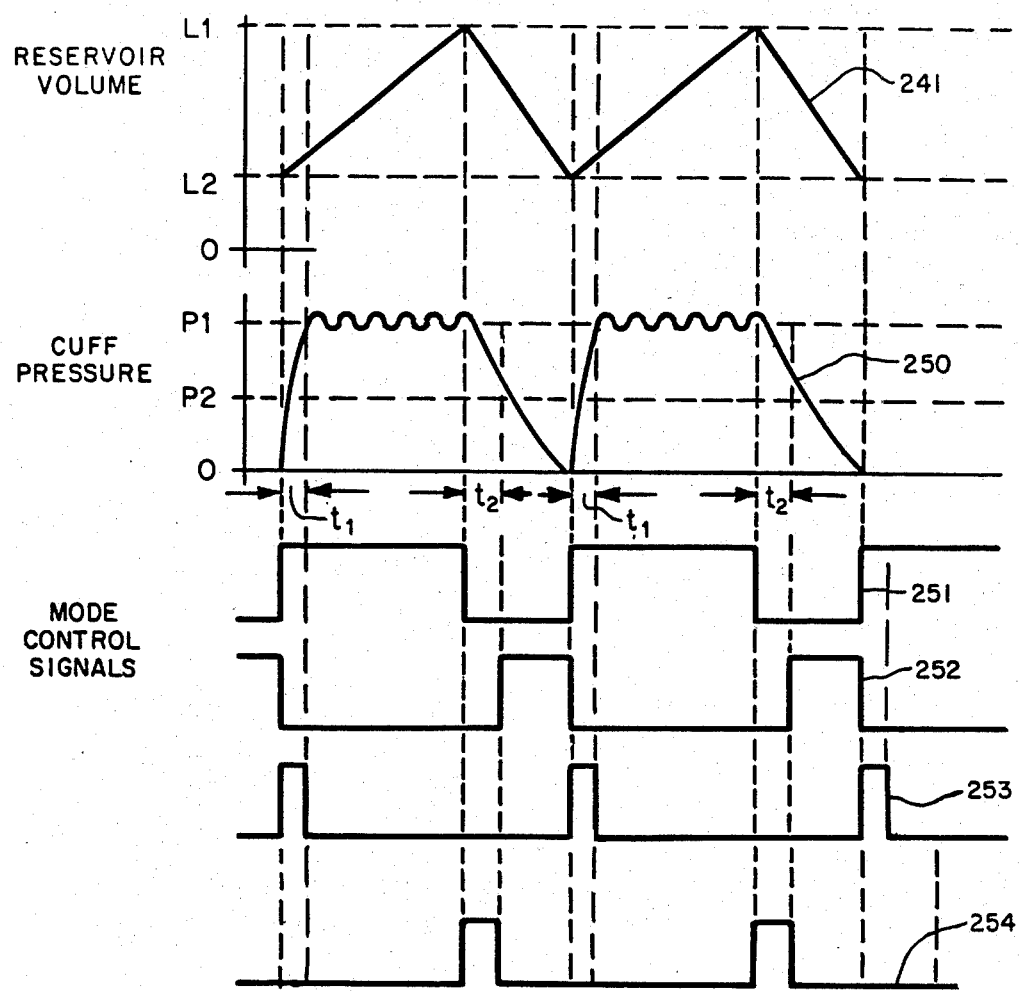
FIG. 12 is a depiction of certain signal waveforms of the blood fractionation apparatus useful in understanding the operation of the system.

The operation of the cuff control circuit is illustrated in FIG. 12. At the beginning of each draw cycle, valve 160 opens and the cuff pressure 250 quickly rises to its nominal level Pl. At this time the cuff mode control signal 251 is logic high, enabling operation of the cuff, and the pump mode control signal 252 is logic low, preventing operation of the pump. For a short time period $t_1$ at the beginning of the draw cycle, as shown by the output 253 of flip-flop 194, the nominal pressure comparator 165 is inhibited to prevent pressure transients from closing the fill valve. For a short predetermined time period $t_2$, at the end of the draw cycle, as shown by the output 254 of flip-flop 196, the output of comparator 180 is inhibited to prevent operation in the return mode until after the time period has passed, notwithstanding the cuff pressure having fallen below the minimum level. This is a safety features which prevents premature return mode operation in the event of a malfunctioning comparator amplifier.

The particular pressure levels and delay periods of the mode and cuff control circuits may be varied as required by a particular application. In a typical single-needle partial recirculation plasmapheresis procedure, such as that described in the previously identified concurrently filed application of Arnold C. Bilstad et al., for example, the cuff may be pressurized to a nominal level of 40 mm. Hg. The dump valve may be set to operate at 100 mm. Hg., and the high pressure alarm may be set for 150 mm. Hg. The low pressure level below which the return cycle commences may be set at 20 mm. Hg. A delay period $t_1$ of one second may be provided at the beginning of each draw cycle, and a delay period $t_2$ of 0.75 second may be provided at the completion of each draw cycle.

Thus, a novel pressure cuff draw mode assist system and method has been described which provides a pressure cuff integrated into a single needle batch-type reversible flow blood fractionation apparatus. The system is entirely automatic, the cuff being automatically actuated in response to fluid volume in an intermediate in-process fluid reservoir, and the apparatus pumps being automatically sequenced to accommodate the pressure cuff.

The pressure cuff draw mode enhancement system of the invention has the further advantage of being dependent only on the volume of separated cellular component, or plasma-deficient whole blood, which is directly related to the volume of whole blood processed; and not to the volume of the collected non-cellular component, or plasma, which is dependent on the hematocrit of the whole blood and therefore not directly related to processed volume. This enables the system to draw and return without readjustment batches of uniform volume from different donors, notwithstanding differences in hematocrits between the donors.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. A control system for a blood fractionation apparatus of the type which separates whole blood into cellular and non-cellular components and utilizes a pressure cuff to increase whole blood collection rate, said system comprising:
   a first fluid reservoir for collecting the cellular component separated from the whole blood:
   a second fluid reservoir for collecting the noncellular component separated from the whole blood;
   means for monitoring the volume of the separated cellular component which is collected in said first fluid reservoir; and
   control means operatively associated with said monitor means for depressurizing the pressure cuff and commencing the return of the separated cellular component from said first fluid reservoir to the donor when the volume of the collected cellular component reaches a predetermined maximum level in said first fluid reservoir, and for pressurizing the pressure cuff and terminating the return of the separated cellular component from said first fluid reservoir to the donor when the volume of the collected cellular component reaches a predetermined minimum level in said first fluid reservoir.

2. A pressure cuff control system as defined in claim 1 wherein said control means are responsive to the weight of the separated cellular component collected in said first fluid reservoir.

3. A pressure cuff control system as defined in claim 2 wherein said control means include an electrical weight transducer providing an output signal indicative of the weight of the separated cellular component collected in said first fluid reservoir.

4. A pressure cuff control system as defined in claim 3 wherein said output signal is an analog signal and said system control means include means for comparing said signal with predetermined maximum and minimum reference levels.

5. A pressure cuff control system as defined in claim 1 wherein said pressure cuff means are operable from an applied pneumatic pressure.

6. A pressure cuff control system as defined in claim 5 including means for maintaining said applied pressure at a predetermined operating level.

7. A pressure cuff control system as defined in claim 5 wherein said control means inhibit return of blood to the donor when said pressure cuff is pressurized above a predetermined level.

8. A pressure cuff control system as defined in claim 1 wherein said control means inhibit the return of blood to the donor for a predetermined delay period following the volume of the separated cellular component reaching said predetermined maximum level in said first fluid reservoir.

* * * * *